(12) United States Patent
Melo (10) Patent No.: US 11,933,162 B2
(45) Date of Patent: Mar. 19, 2024

(54) CALIBRATING EROSIONAL SAND PREDICTION

(71) Applicant: Landmark Graphics Corporation, Houston, TX (US)

(72) Inventor: Raphael de Souza Gonzalez Melo, Houston, TX (US)

(73) Assignee: Landmark Graphics Corporation, Houston, TX (US)

(*) Notice: Subject to any disclaimer, the term of this patent is extended or adjusted under 35 U.S.C. 154(b) by 37 days.

(21) Appl. No.: 17/529,692

(22) Filed: Nov. 18, 2021

(65) Prior Publication Data

US 2022/0365062 A1 Nov. 17, 2022

Related U.S. Application Data

(60) Provisional application No. 63/185,049, filed on May 6, 2021.

(51) Int. Cl.
| | |
|---|---|
| *E21B 47/06* | (2012.01) |
| *E21B 47/10* | (2012.01) |
| *G01N 33/28* | (2006.01) |
| *E21B 43/10* | (2006.01) |

(52) U.S. Cl.
CPC .............. *E21B 47/06* (2013.01); *E21B 47/10* (2013.01); *G01N 33/2823* (2013.01); *E21B 43/105* (2013.01); *E21B 2200/20* (2020.05)

(58) Field of Classification Search
CPC ...... E21B 47/06; E21B 2200/20; E21B 33/00; G01N 33/2835
See application file for complete search history.

(56) References Cited

U.S. PATENT DOCUMENTS

| | | | |
|---|---|---|---|
| 7,143,826 B2 | 12/2006 | Nguyen et al. | |
| 7,653,488 B2 * | 1/2010 | Mese | E21B 43/00 |
| | | | 702/50 |

(Continued)

FOREIGN PATENT DOCUMENTS

| | | |
|---|---|---|
| EP | 2478457 | 6/2019 |
| WO | 2017223483 | 12/2017 |
| WO | 2021052604 | 3/2021 |

OTHER PUBLICATIONS

Pham, "Estimation of Sand Production Rate Using Geomechanical and Hydromechanical Models", Hindawi, Advances in Material Science and Engineering, vol. 2017, Article ID 2195404, 2017, 11 pages.

(Continued)

*Primary Examiner* — Catherine Loikith
(74) *Attorney, Agent, or Firm* — Kilpatrick Townsend & Stockton LLP (57) ABSTRACT

A system may include a processing device and a memory device that includes instructions to receive real-time data including wellhead pressure, a new sand measurement, and a new erosion rate for a wellbore. A model including an available reference sand rate for the wellbore based on the wellhead pressure and at least one of the new sand measurement or the new erosion rate of the wellbore may be calibrated. The model may be applied to determine a calibrated sand rate is within a pre-determined threshold. A new sand production rate for the wellbore based on the model may be determined.

17 Claims, 5 Drawing Sheets

(56) References Cited

U.S. PATENT DOCUMENTS

| | | | | |
|---|---|---|---|---|
| 7,711,486 B2 * | 5/2010 | Thigpen | ................ | E21B 43/128 |
| | | | | 702/9 |
| 8,534,114 B2 * | 9/2013 | Ellson | ................... | E21B 47/107 |
| | | | | 73/1.82 |
| 2013/0008649 A1 | 1/2013 | Vestbostad et al. | | |

OTHER PUBLICATIONS

TRS Energy Consultants, Ltd., "Sand Production Option in QLIII", Nov. 2008, 24 pages.
Application No PCT/US2021/059884, International Search Report and Written Opinion, dated Mar. 10, 2022, 10 pages.

* cited by examiner

CALIBRATING EROSIONAL SAND PREDICTION

CROSS REFERENCE TO RELATED APPLICATION

This claims priority to U.S. Application No. 63/185,049, titled "Calibrating Erosional Sand Prediction" and filed May 6, 2021, the entirety of which is incorporated herein by reference.

TECHNICAL FIELD

The present disclosure relates generally to wellbore operations and, more particularly (although not necessarily exclusively), to applying a model for calibrating sand rate within a wellbore.

BACKGROUND

Wellbore operations and operating conditions for a well production environment may cause sand flow during a production operation. Such operation conditions may include wellhead flowing pressure and bottom hole pressure. Sand flow may indicate erosion of the wellbore, and erosion rate may be measured by downhole tools. Since wellbore stability can be negatively affected from erosion, operating parameters may be adjusted in response to the erosion measurement. But, measuring these conditions alone during production may not assist in effectively managing wellbore stability.

DETAILED DESCRIPTION

Certain aspects and examples of the present disclosure relate to calibrating a sand erosional model with an available sand production rate, via a new sand measurement taken from a wellbore during a well operation. A calibrated sand erosional model can be used to predict a new sand production rate or inflow performance relationship (IPR) of a wellbore within a threshold and more accurately. The sand IPR can be the relationship between the sand production rate and bottomhole pressure in the wellbore. The erosional model can be a computer model for predicting the flow of sand into the wellbore. The model can leverage or use a reservoir simulator that accounts for the solid phase of the wellbore. The well operation can be a production operation or any other suitable well operation. The sand production rate can be an estimated amount of sand occurring in the wellbore over time.

Examples of issues that stem from erosion in wells can include loss of the well and lines in the surface of the well. The issues can be caused by wells producing sand. Some technologies may not estimate sand rates in well environments to combat erosion issues. Other technologies may not calibrate the sand rate, or even those that measure sand flow in wells may not account for solid phase of the wellbore when determining sand flow measurements in well environments. Certain examples of a system according to the present disclosure can use a calibrated model for estimating sand production rates, take measurements of flow in the subsurface well environment, and use reservoir simulators as well models that account for the solid phase of a wellbore. A system may also improve sand separation operations during wellbore operations by assessing a material balance of sand accumulation in the wellbore. Wellbore operations teams can be enabled to manage a well field to avoid issues due to erosion.

In some examples, a model can receive a new sand production measurement for a well. The model can execute a calibration on the available sand rate using a calibration algorithm. Once the model is calibrated, the model can determine a new sand production rate and a sand-free operating envelope. The model can output a command to adjust a setting of a well tool used in the wellbore operation based on the new sand production rate. The new sand production rate and sand-free operating envelope can be a guide demonstrating a region within which the well tool of the operation may operate.

In some examples, the system can take flow measurements of subsurface environments either indirectly (e.g. as erosion rate) or directly (e.g. the sand rate). In some examples, the model can take account of the mass generation term and its associated relevant variables for a reliable calibration with results within the threshold. In some examples, the model can give sand rate estimation per well, given real-time wellhead flowing pressure and available sand rate. In some examples, the main model can run a Simplified Representative Elementary Volume (SREV) model to adjust the available sand rate based on the reservoir simulator that accounts for the solid phase of the wellbore.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

Figure 1:
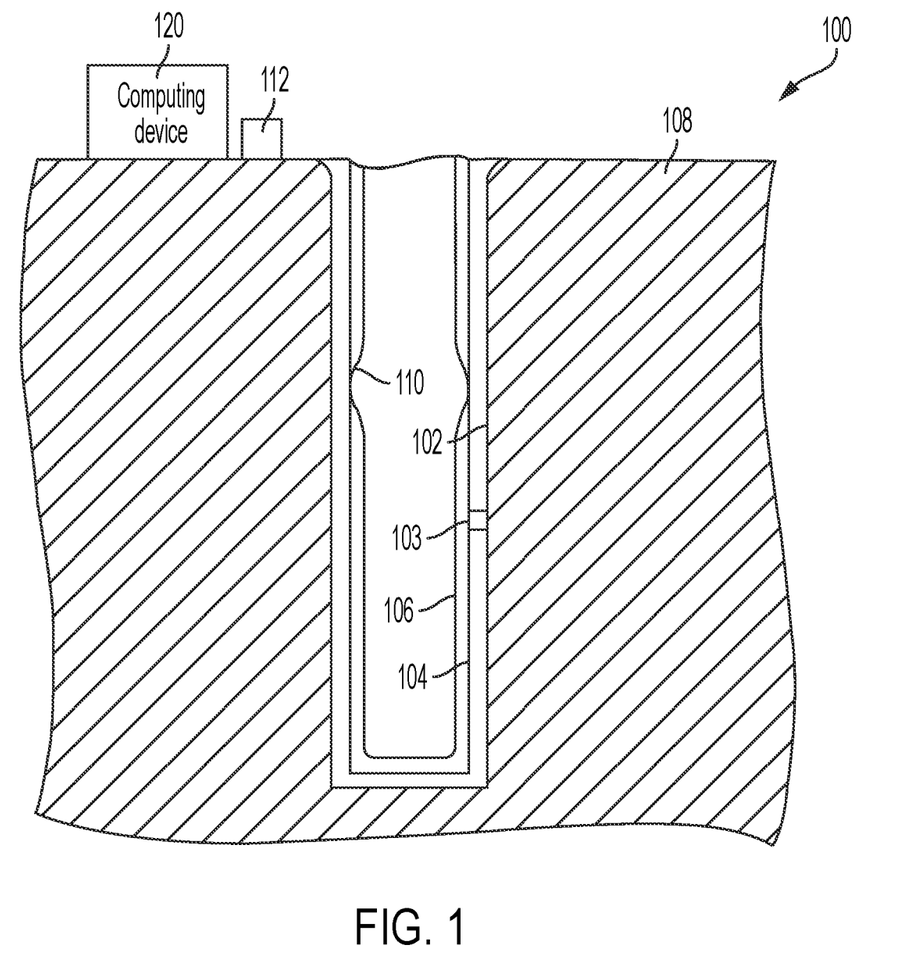
FIG. 1 is a schematic of an example of a well production environment that can implement a sand erosional calibration model for predicting an amount of sand in a wellbore according to one example of the present disclosure.

FIG. 1 is a schematic of an example of a well production environment that can implement a sand erosional calibration model for predicting an amount of sand in a wellbore according to one example of the present disclosure.

Once the model is calibrated, the model can determine a new sand production rate and a sand-free operating envelope. The model can output a command to adjust a setting of a well tool used in the wellbore operation based on the new sand production rate. The new sand production rate and sand-free operating envelope can be a guide demonstrating a region within which the well tool of the operation may operate.

During a production operation, the wellbore tubular 104, which may be a casing or a tubing, can be positioned within a wellbore 102. The wellbore 102 can be formed below a surface 108 in a subterranean formation. Prior to positioning the wellbore tubular 104 within the wellbore 102, the wellbore tubular 104 can have a same inner diameter along the entire length of the wellbore tubular 104. Once the wellbore tubular 104 is positioned at a desired length within the wellbore 102, an expansion tool 106 can be deployed downhole within the wellbore tubular 104. The expansion tool 106 can include one or more expanded portions 110 that can enlarge portions of the wellbore tubular 104. The changes in the inner diameter along the wellbore tubular by the expansion tool 106 can cause reflections of pressure pulses that can be used to monitor fluid flow in the wellbore. In other examples, a well system can use any other suitable embodiment for a fluid control assembly. A fluid control assembly can be located in any portion of the well system, including in a substantially vertical portion of a well system that is only a substantially vertical well system or that also includes a deviated portion. Any number of fluid flow control assemblies can be used in a well system, including one fluid flow control assembly that can control flow in one zone or in more than one zone.

The wellbore system 100 can include a computing device 120 disposed at the surface 108 of a subterranean formation, as well as the equipment 103. The equipment 103 can be disposed in the wellbore 102 and can be disposed in a reservoir. It should be noted that while the wellbore 102 is shown as a vertical wellbore, the wellbore 102 can additionally or alternatively have a substantially horizontal section in which equipment 103 is located. A sensor 112 can be communicatively coupled to the equipment 103 disposed in the wellbore 102 and the reservoir, and the sensor 112 can be communicatively coupled to the computing device 120.

The computing device 120 can receive data from the sensor 112. The data from the sensor 112 can be received from the equipment 103 disposed in the wellbore 102 and the reservoir during a well operation. The real-time data can include characteristics of the reservoir such as viscosity, velocity and fluid pressure as these quantities spatially vary. The data associated with the reservoir can be used to enable a sand calibration engine to calibrate an available sand rate based on the data in computing device 120. In the example of FIG. 1, data from the wellbore 102 can be stored in database stores associated with the corresponding wellbore 102. The wellbore 102 is illustrated as operating in isolation with data considered real-time since the data can be collected as wellbore equipment 103 is being operated. In another example, a dataset can be acquired from a second wellbore (not pictured in FIG. 1) and used to calibrate an available sand rate based on the data from the second wellbore.

The computing device 120 can include a processor interfaced with other hardware via a bus. A memory, which can include any suitable tangible (and non-transitory) computer-readable medium, such as random-access memory ("RAM"), read-only memory ("ROM"), electrically erasable and programmable read-only memory ("EEPROM"), or the like, can embody program components that configure operation of the computing device 120. In some aspects, the computing device 120 can include input/output interface components (e.g., a display, printer, keyboard, touch-sensitive surface, and mouse) and additional storage.

Figure 2:
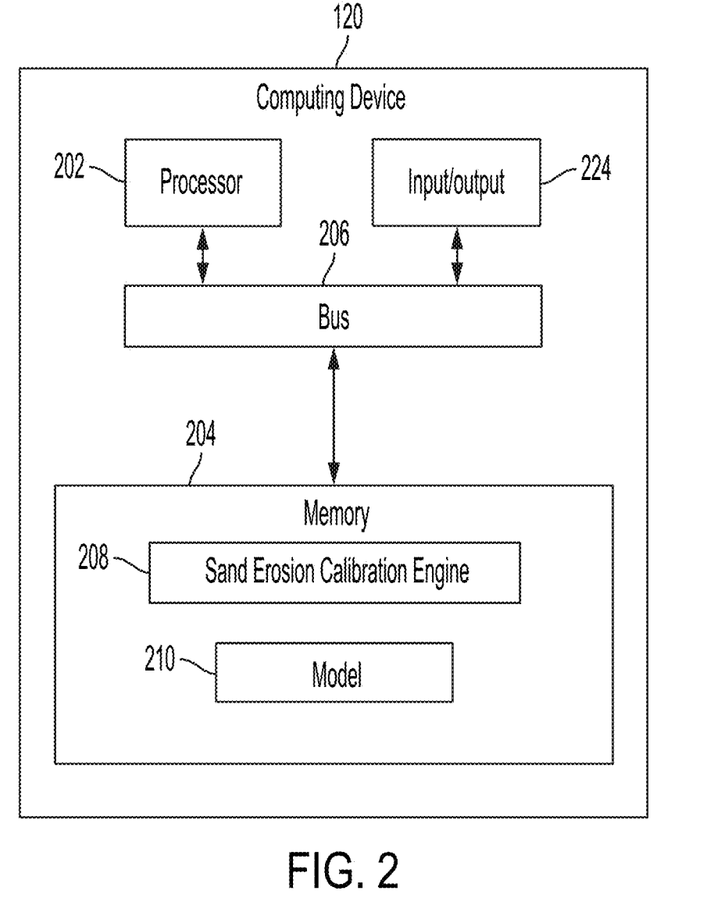
FIG. 2 is a block diagram of an example of a system for predicting an amount of sand in a wellbore within a threshold during well operations according to one example of the present disclosure.

FIG. 2 is a block diagram of an example of a system for predicting an amount of sand in a wellbore within a threshold during well operations according to one example of the present disclosure.

The system can include a computing device 120 having a processor 202, a bus 206, a memory 204, and a display device 224. In some examples, the components shown in FIG. 2 can be integrated into a single structure. For example, the components can be within a single housing with a single processing device. In other examples, the components shown in FIG. 2 can be distributed (e.g., in separate housings) and in electrical communication with each other using various processors. It is also possible for the components to be distributed in a cloud computing system or grid computing system.

The processor 202 can be communicatively coupled to the memory 204 via the bus 206. The non-volatile memory 204 may include any type of memory device that retains stored information when powered off. Non-limiting examples of the memory 204 include EEPROM, flash memory, or any other type of non-volatile memory. In some examples, at least part of the memory 204 can include a medium from which the processor 202 can read instructions. A computer-readable medium can include electronic, optical, magnetic, or other storage devices capable of providing the processor 202 with computer-readable instructions or other program code. Non-limiting examples of a computer-readable medium include (but are not limited to) magnetic disk(s), memory chip(s), ROM, RAM, an ASIC, a configured processor, optical storage, or any other medium from which a computer processor can read instructions. The instructions can include processor-specific instructions generated by a compiler or an interpreter from code written in any suitable computer-programming language, including, for example, C, C++, C#, etc.

The memory 204 can contain sand calibration engine 208 and a model 210. The computing device 120 can execute sand calibration engine 208 to execute the model 210. The sand calibration engine 208 can include instructions for calibrating the available sand rate based on the data stored in computing device 120. The model 210 can be the calibration model for estimating an amount of sand in a wellbore. The instructions can include instructions for adjusting parameters of the model 210. Once the inputs of the model 210 are calibrated and the output of the model 210 is within a predetermined threshold, the calibration engine 208 can include instructions to determine a new sand production rate and a sand-free operating envelope. The calibration engine 208 can also output a command to adjust a setting of a well tool used in the wellbore operation based on the determination of the new sand production rate or sand-free operating envelope. The output of the model 210 can be shown on the display device 224. Examples of the display device can include a communication port for communicating data to on-site or off-site device or any other suitable device.

Figure 3:
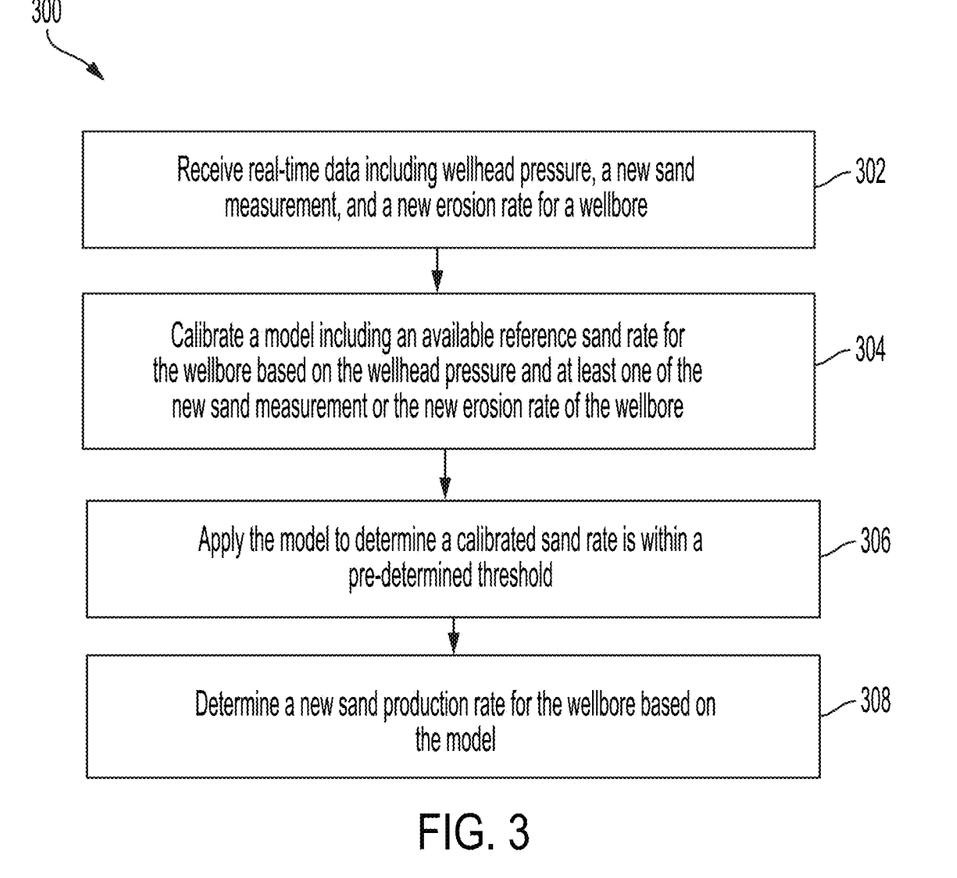
FIG. 3 is a flow chart of an example of a sand erosional calibration model predicting an amount of sand in a wellbore within a threshold during well operations according to one example of the present disclosure.

FIG. 3 is a flow chart of an example method 300 of a sand erosional calibration model predicting an amount of sand in a wellbore within a threshold during well operations according to one example of the present disclosure.

At block 302, the system can receive real-time data including a new sand measurement for the wellbore during a well operation. Real-time data stored in the computing device 120 can be received via a cloud platform (e.g., Google Cloud Platform).

At block 304, the system can calibrate a model including a reference sand rate for the wellbore based on the new sand measurement of the wellbore. The system may have access to a number of previously calibrated models. The models can be used for available sand rates.

At block 306, the system can apply the model to determine a calibrated sand rate is within a pre-determined threshold. The model may compare the difference between a reference sand rate and a newly calculated sand rate via a calibration algorithm. The calibration algorithm may loop through until the model reaches the threshold.

At block 308, the system can determine a new sand IPR for the wellbore based on the model. The output may be saved in a database store with previously calibrated sand rates.

Figure 4:
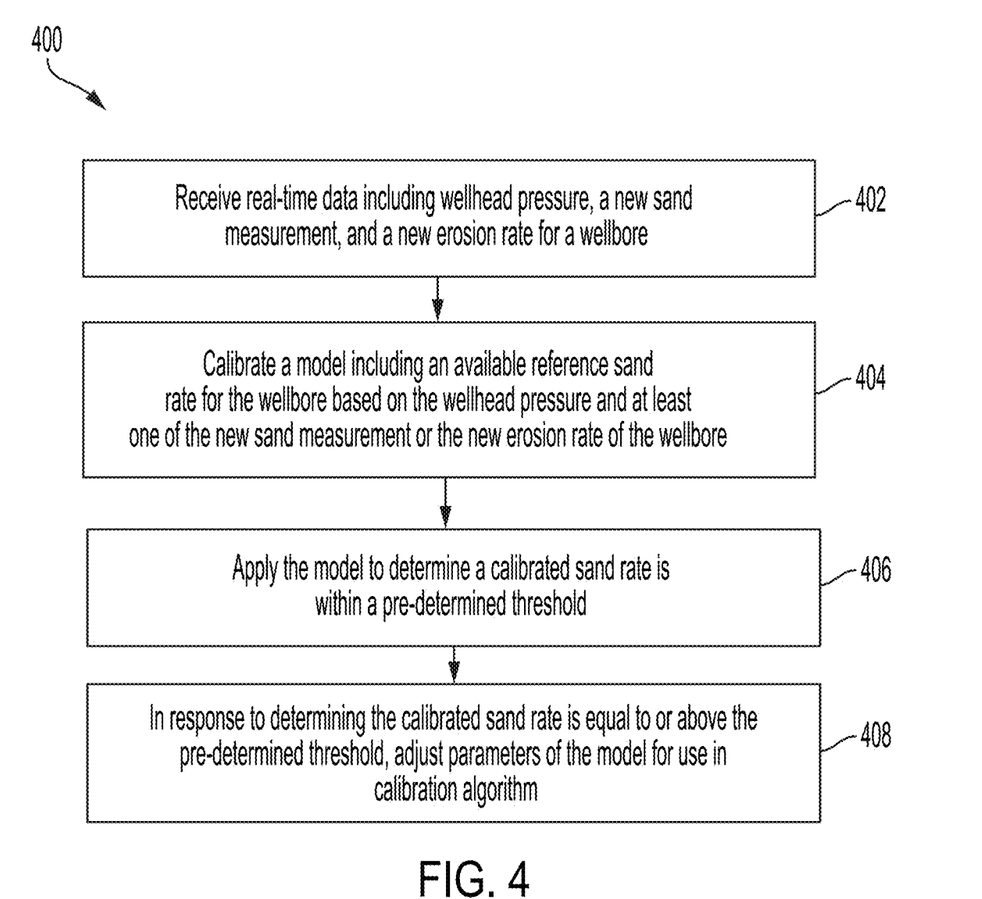
FIG. 4 is a process flow of an example of an algorithm for calibrating the sand rate within a pre-determined threshold according to one example of the present disclosure.

FIG. 4 is a process flow of an example method 400 using an algorithm for calibrating the sand rate within a pre-determined threshold according to one example of the present disclosure.

At block 402, the computing device 120 can receive real-time data including wellhead pressure, a new sand measurement, and a new erosion rate for a wellbore. In some examples, the calibration engine 208 can get a well list from a Sand Clamp-On test table. The calibration engine 208 can retrieve data for each well from the corresponding database for the well. The types of data for the well can include prior calibrated models, subsurface flow information, or other qualities of the formation. The computing device 120 may retrieve available well data for use in calculating sand data or generating calibration models. In some examples, the real-time data can be received by a Google Cloud Platform (GCP) environment. The real-time data can be received by bit queries. The data can then be obtained by querying the GCP. Wellhead pressure, erosion rate, and other data can be measured from the well field. The wellhead pressure and other data can be read to the cloud. Other data may include bottom hole pressure, well head flowing pressure, or any other suitable operating conditions used in production of a wellbore or well field. In some examples, the well data can be stored separately for each well. New sand measurement data can include erosion rate or other suitable sand measurements for assessing the sand rate at the solid phase of the wellbore. Other tool or formation data can include bottom hole pressure, wellhead flowing pressure, and any other suitable data for assessing the sand rate of the solid phase of the wellbore.

In particular, data can be received from a currently operating wellbore. Wellhead pressure and reference sand rate can be data stored (e.g., in real-time) for each well. The reference sand rate can be determined from the erosion rate. In some examples, each currently operating wellbore can have a work process in the GCP that reads the erosion rate from the well field (e.g., in real-time) and calculates the reference sand rate from the erosion rate. In an example, such a calculation for the reference sand rate may be calculated by a formula, such as the Salamar equation. In some examples, the work process may include calculating the reference sand rate from another suitable new sand measurement from the wellbore. In some examples, the reference sand rate may be updated (e.g., real-time) when the new sand measurement is taken for the wellbore.

At block 404, the system can calibrate a model including an available reference sand rate for the wellbore based on the wellhead pressure and at least one of the new sand measurement or the new erosion rate of the wellbore.

The Simplified Representative Elementary Volume (SREV) model can show co-existence of phases of a wellbore. The model can include a representative elementary volume that can include the fluid, fluidized solid, and solid volume within the wellbore, which can be used to generate a phase diagram of the same. The model can then be calibrated. The SREV calibrator can be used to calibrate input data, such as clamp on data and any data from intrusive probes. The model can be saved.

In some examples, SREV models may be generated (e.g., in real-time) with available well data. For example, SREV models can be generated by capturing the corresponding well data and writing the input files that compose the SREV model. In some examples, the system can calculate a quantity Sm/d for each well. Sm/d can be a relationship between a mass, mixture velocity, erosional rate, mixture density, and diameter of the well or subsurface formation. For example, Sm/d can be calculated using the Salamar equation via the following formula:

$$\left(\frac{s_m}{d}\right)i = \frac{W_i \cdot v_{mi}^2}{ER_i \cdot \rho_{mi} \cdot D^2},$$

where Wi is the mass, vmi is the mixture velocity, ERi is the erosional rate, ρmi is the mixture density and D is the diameter. The Salamar equation can be used to calculate the reference sand rate.

The system can calculate a reference sand rate (Qs·ref) for each well. For example, the computing device can receive the new sand measurement from a well tool and an available sand rate from a database store associated with the wellbore and apply the model to calculate Qs·ref (e.g., in real time). In some examples, the calculation of Qs·ref can depend on a type of the new sand measurement (e.g. viscosity, amount, erosional rate) or the calculation of Sm/d.

In some examples, the system can check if a flag>0 is true. The flag can have a value that indicates what data is available for each well and additionally, what data is available from the surface network hydraulic model, or reservoir simulator (e.g., Nexus). For example, flag=0 can indicate there is only an erosion rate available from real-time data (i.e., no clamp-on history or Nexus results), and may indicate the system may not have enough data to calibrate the current SREV model. The complete table to identify the flags is in table 1.

TABLE 1

| Flag Number | Clamp-on history | Erosion Rate | Nexus results |
|---|---|---|---|
| 0 | No | Yes | No |
| 1 | No | Yes | Yes |
| 3 | No | No | Yes |
| 3 | No | No | No |
| 1 | Yes | Yes | Yes |
| 1 | Yes | No | No |
| 1 | Yes | No | Yes |
| 1 | Yes | Yes | No |

Upon determining flag>0 is true, the system can copy SREV models generated from the well data. In some examples, the SREV model can be calibrated at the time the SREV is generated. In some examples, a model can be created manually upon determining flag>0 is true and may be calibrated then. Alternatively, upon determining flag>0 is false, the system can copy calibrated models from an Approved Model folder. The models of the Approved Model folder can be associated with a type of a wellbore or a location with a nearby wellbore in proximity to the well of interest.

Additionally, the system can check if an expression bottom hole pressure (BHP) calculation success? is true. The system can check if flag<3 is true, upon determining BHP calculation success? is true. For example, the flag value can indicate data for the well as represented above in Table 1. Having the BHP calculation, the system can carry out next steps for determining Qs·calc. Alternatively, upon determining BHP calculation success? is false, the system can copy a sand IPR curve from a last approved model, which can be used to determine Qs·calc.

At block 406, the system can apply the model to determine a calibrated sand rate is within a pre-determined threshold. For example, the SREV model can determine Qs·calc. Upon determining the flag<3 is true, or after saving the calibrated models (whichever comes first), the system can run the SREV model and save Qs as a calibrated reference sand rate, Qs, in the Approved Model folder. This can indicate there is sufficient information for the model to determine a calculated sand rate using the model. For example, once the calibrated sand rate, Qs, is achieved it can be the calculated sand rate used in conjunction with sand saturation values in the SREV model for carrying out a calibration algorithm to determine an error value within a threshold. Alternatively, upon determining flag<3 is false (e.g., only Nexus results are available), the system can run models to determine the calculated sand rate (Qs·calc) and calibrate the calculated sand rate. The calculated sand rate can be determined at least in part based on the received BHP calculation. With Qs·calc, the system can then check if |Qs·calc−Qs·ref|<ε is true. For example, ε can be the pre-determined threshold. In some examples, ε can be calculated by the model. The model can run four parameters (e.g., Qs·ref, Qs·calc, new sand measurement, and erosion coefficient) for determining the calculated sand rate is within the threshold, as described with further detail with respect to FIG. 5. Upon determining |Qs·calc−Qs·ref|<ε is true, the system can save the calibrated models. The calibrated models can be saved in an Approved Model storage according to a type of the wellbore.

At block 408, in response to determining the calibrated sand rate is equal to or above the pre-determined threshold, adjust parameters of the model for use in calibration algorithm. An example of a calibration algorithm can include executing the SREV model. The SREV model can be run multiple times. For example, the Qs·calc can be calculated at least in part based on the BHP calculation. Initially, Qs·calc can be an initial calculated sand rate that is dependent on the calculation being tested for being within a pre-determined threshold of the Qs·ref. If Qs·calc is not within the threshold, the parameters of the model can be adjusted to recalculate Qs·calc and determine Qs·calc within the error threshold. Upon determining |Qs·calc−Qs·ref|<ε is false, the system can adjust the four parameters of the model to do calibration. For example, the parameters can be adjusted by applying a correction factor to the parameter or taking an average for the parameter.

In some examples, the system can complete a sensitivity analysis on well head flowing pressure (WHFP). For example, the sensitivity analysis can quantify different independent values of WHFP and their effect on the outcome of the dependent variable. In some examples, the system can generate WHFP IPR curves, after completing a sensitivity analysis using the WHFP or after copying an existing sand IPR curve from the last sand IPR approved model. For example, the WHFP IPR curves may be stored in a database or displayed on an output device. In some examples, the system can copy NETool models generated from the types of data for the well, such as prior calibrated models, subsurface flow information, other qualities of the formation, or generated SREV models. For example, the NETool models may include a mesh of nodes of the completion and near wellbore region. Additionally or alternatively, the system can generate BHP IPR curves. For example, the BHP IPR curves may be stored in a database or displayed on an output device.

Figure 5:
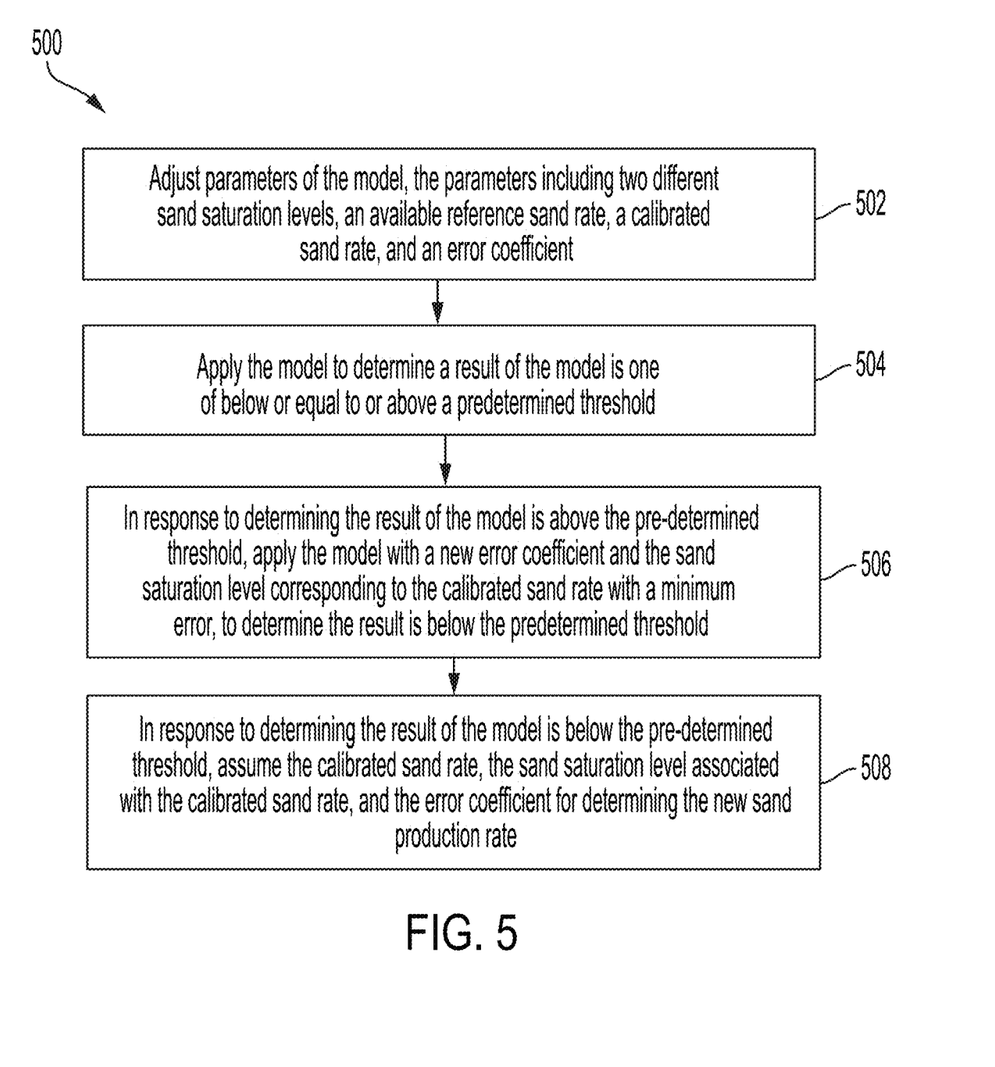
FIG. 5 is a process flow of an example of an algorithm for calibrating the sand rate within a pre-determined threshold according to one example of the present disclosure.

FIG. 5 is a process flow 500 of an example of an algorithm for calibrating the sand rate within a pre-determined threshold according to one example of the present disclosure.

At block 502, a system can adjust parameters of the model, the parameters including two different sand saturation levels, an available reference sand rate, a calibrated sand rate, and an erosion coefficient. Initially, the model can be run multiple times using different levels of sand saturation (SAND_SAT) levels—for example a low, medium, and high sand saturation level. The system can determine the sand saturation levels. An example of a low sand saturation level can be 0.0001, or a range not equal to 0. An example of a medium sand saturation level is 0.5. An example of a high sand saturation level is 0.9999, or a range not equal to 1. The outputs of the three sand saturation values tested can be used as boundaries (e.g., middle and end points) in a quadratic function. The calculated or calibrated sand rates from a simulator file (e.g., ".frc" file) and the sand saturation levels tested can then be used to generate (e.g., by fitting a regression) a quadratic function, where y-axis are the calculated or calibrated sand rates from the reservoir simulator file and x-axis are the sand saturation level values tested. Thus, the quadratic function can determine the calibrated available sand rate according to an adjustment of the sand rate based on the new sand measurement Further, the model can find the coefficients of the quadratic function $y=ax2+bx+c-D$, where D is the reference sand rate. Thus, the function can give the error between the adjusted sand rate and the reference sand rate.

At block 504, the system can apply the model to determine a result of the model is below a predetermined threshold. In an additional run of the model, the model can calculate roots x and x2 of the quadratic equation $y=ax2+bx+c$. The roots can be used as the sand saturation levels with which to find two different results of the calculated or calibrated sand rate, Qs·calc (e.g. case A and case B). The model can run as inputs the Qs·calcs, Qs·ref, sand saturation levels, and erosion coefficient, where Qs·calc is the calculated sand rate, and Qs·ref is the reference sand rate. The calibration algorithm can execute the SREV model, with sand saturation levels equal to x and x2 and with an initial erosion coefficient of 1, to obtain the two different results Qs·calc (e.g. case A and case B). The result of the calibration algorithm can be the error between each of the values of Qs·calc and Qs·ref (e.g. error A and error B). The model can determine whether either error A or B are below a pre-determined threshold, and the calibration algorithm can assume the Qs·calc with a minimum error for determining the new sand production rate. The model can then determine the new sand production rate.

At block 506, in response to determining the result of the model is above the pre-determined threshold, the system can apply the model with a new erosion coefficient and the sand saturation level corresponding to the calibrated sand rate with the minimum error, to determine the result is below the predetermined threshold. For example, if both errors A and B are equal to or greater than the threshold, then the algorithm can assume the sand saturation level associated with the Qs·calc with the minimum error and an erosion coefficient of $$\frac{Qs.calc}{Qs.ref},$$

run the SREV model, and compare against the threshold. The algorithm may continue to run the SREV model according to blocks 502 through 506 and compare the results until the new error is less than the threshold according to the following variations of the sand saturation level (consider all the results already calculated for SAND_SAT) and the abovementioned criteria for the erosion coefficient. The algorithm can run the SREV model with a new SAND_SAT that is the middle point of the low SAND_SAT and SAND_SATk (where SAND_SATk is the closest to SAND_SAT1). The algorithm can run the SREV model with a new SAND_SAT that is the middle point of the medium SAND_SAT and SAND_SATm (where SAND_SATm is the closest to SAND_SAT3).

At block 508, in response to determining the errors A and B are below the pre-determined threshold, the model can assume the calibrated sand rate, the sand saturation level associated with the calibrated sand rate, and the erosion coefficient, for determining the new sand production rate. The model can then determine the new sand production rate. For example, the new sand production rate can be determined based on the sand rate.

According to the above example, the equation $y=ax2+bx+c$ may be the calculated sand rate according to an adjustment of the sand rate based on the new sand measurement that is the SAND_SAT. Alternatively, the model may calibrate sand rate based on any other suitable variable for assessing the sand rate at the solid phase of the wellbore. In some examples, the erosion coefficient, ER_COEF, of the SREV model may be determined based on an error of the sand rate being within the threshold.

In some aspects, a system, method, and medium for applying a model for calibrating sand rate within a wellbore are provided according to one or more of the following examples:

Example 1 is a system comprising: a processing device; and a memory device that includes instructions executable by the processing device for causing the processing device to: receive real-time data including wellhead pressure, a new sand measurement, and a new erosion rate for a wellbore; calibrate a model including an available reference sand rate for the wellbore based on the wellhead pressure and at least one of the new sand measurement or the new erosion rate of the wellbore; apply the model to determine a calibrated sand rate is within a pre-determined threshold; and determine a new sand production rate for the wellbore based on the model.

Example 2 is the system of example(s) 1, wherein the memory device further includes instructions executable by the processing device for causing the processing device to: output a command to adjust a setting of a well tool used in a wellbore operation based on the new sand production rate.

Example 3 is the system of example(s) 1, wherein the instructions executable by the processing device for causing the processing device to apply the model to determine the calibrated sand rate is within the pre-determined threshold includes: determining two different results for the calibrated sand rate using two different sand saturation levels and an initial erosion coefficient; and determining one of the two different results of the model is below the pre-determined threshold.

Example 4 is the system of example(s) 3, wherein the model is configurable to calculate initial sand saturation levels, wherein the initial sand saturation levels are configurable to be roots of a quadratic relationship between sand saturation level values and available sand rate values from a reservoir simulator.

Example 5 is the system of example(s) 3, wherein the memory device further includes instructions executable by the processing device for causing the processing device to: in response to determining any of the results of the model is below the pre-determined threshold: assume the calibrated sand rate, the sand saturation level associated with the calibrated sand rate, and the erosion coefficient for determining the new sand production rate.

Example 6 is the system of example(s) 3, wherein the instructions executable by the processing device for causing the processing device to apply the model to determine the calibrated sand rate is within the pre-determined threshold includes: optionally determining one of the two different results of the calibrated sand rate is equal to or above the pre-determined threshold, and the memory device further includes instructions executable by the processing device for causing the processing device to: in response to determining one of the two different results of the model is equal to or above the pre-determined threshold: apply the model using the calibrated sand rate with a minimum error, the sand saturation level associated with the calibrated sand rate with the minimum error, and a new erosion coefficient; and determine the result of the model is below the pre-determined threshold.

Example 7 is the system of example(s) 6, wherein the instructions executable by the processing device for causing the processing device to apply the model to determine the calibrated sand rate is within the pre-determined threshold further includes: optionally determining the result of the model using the calibrated sand rate with the minimum error is equal to or above the pre-determined threshold, and the memory device further includes instructions executable by the processing device for causing the processing device to: in response to determining the result of the model using the calibrated sand rate with the minimum error is equal to or above the pre-determined threshold: re-apply the model using the calibrated sand rate with the minimum error, two new sand saturation levels, and the initial erosion coefficient for determining the two different results, until the error of the calibrated sand rate is below the pre-determined threshold.

Example 8 is a method comprising: receiving real-time data including wellhead pressure, a new sand measurement, and a new erosion rate for a wellbore; calibrating a model including an available reference sand rate for the wellbore based on the wellhead pressure and at least one of the new sand measurement or the new erosion rate of the wellbore; applying the model to determine a calibrated sand rate is within a pre-determined threshold; and determining a new sand production rate for the wellbore based on the model.

Example 9 is the method of example(s) 8, further comprising: outputting a command to adjust a setting of a well tool used in a wellbore operation based on the new sand production rate.

Example 10 is the method of example(s) 8, wherein applying the model to determine the calibrated sand rate is within the pre-determined threshold includes: determining two different results for the calibrated sand rate using two different sand saturation levels and an initial erosion coefficient; and determining one of the two different results of the model is below the pre-determined threshold.

Example 11 is the method of example(s) 10, wherein the model is configurable to calculate initial sand saturation levels, wherein the initial sand saturation levels are configurable to be roots of a quadratic relationship between sand saturation level values and available sand rate values from a reservoir simulator.

Example 12 is the method of example(s) 10, further comprising: in response to determining any of the results of the model is below the pre-determined threshold: assuming the calibrated sand rate, the sand saturation level associated with the calibrated sand rate, and the erosion coefficient for determining the new sand production rate.

Example 13 is the method of example(s) 10, wherein applying the model to determine the calibrated sand rate is within the pre-determined threshold includes: optionally determining one of the two different results of the calibrated sand rate is equal to or above the pre-determined threshold; and in response to determining the result of the model using the calibrated sand rate with the minimum error is equal to or above the pre-determined threshold: re-applying the model using the calibrated sand rate with the minimum error, two new sand saturation levels, and the initial erosion coefficient for determining the two different results, until the error of the calibrated sand rate is below the pre-determined threshold.

Example 14 is the method of example(s) 13, wherein applying the model to determine the calibrated sand rate is within the pre-determined threshold includes: optionally determining the result of the model using the calibrated sand rate with the minimum error is equal to or above the pre-determined threshold; and in response to determining the result of the model using the calibrated sand rate with the minimum error is equal to or above the pre-determined threshold: re-apply the model using the calibrated sand rate with the minimum error, two new sand saturation levels, and the initial erosion coefficient for determining the two different results, until the error of the calibrated sand rate is below the pre-determined threshold.

Example 15 is a non-transitory computer-readable medium comprising instructions that are executable by a processing device for causing the processing device to perform operations comprising: receiving real-time data including wellhead pressure, a new sand measurement, and a new erosion rate for a wellbore; calibrating a model including an available reference sand rate for the wellbore based on the wellhead pressure and at least one of the new sand measurement or the new erosion rate of the wellbore; applying the model to determine a calibrated sand rate is within a pre-determined threshold; and determining a new sand production rate for the wellbore based on the model.

Example 16 is the non-transitory computer-readable medium of example(s) 15, wherein the operations further comprise: outputting a command to adjust a setting of a well tool used in a wellbore operation based on the new sand production rate.

Example 17 is the non-transitory computer-readable medium of example(s) 15, wherein the operation of applying the model to determine the calibrated sand rate is within the pre-determined threshold includes: determining two different results for the calibrated sand rate using two different sand saturation levels and an initial erosion coefficient; and determining one of the two different results of the model is below the pre-determined threshold.

Example 18 is the non-transitory computer-readable medium of example(s) 15, wherein the model is configurable to calculate initial sand saturation levels, wherein the initial sand saturation levels are configurable to be roots of a quadratic relationship between sand saturation level values and available sand rate values from a reservoir simulator.

Example 19 is the non-transitory computer-readable medium of example(s) 15, wherein the operations further comprise: in response to determining any of the results of the model is below the pre-determined threshold: assuming the calibrated sand rate, the sand saturation level associated with the calibrated sand rate, and the erosion coefficient for determining the new sand production rate.

Example 20 is the non-transitory computer-readable medium of example(s) 15, wherein the operation of applying the model to determine the calibrated sand rate is within the pre-determined threshold includes: applying the model to determine the calibrated sand rate is within the pre-determined threshold includes: optionally determining one of the two different results of the calibrated sand rate is equal to or above the pre-determined threshold; and in response to determining the result of the model using the calibrated sand rate with the minimum error is equal to or above the pre-determined threshold: re-applying the model using the calibrated sand rate with the minimum error, two new sand saturation levels, and the initial erosion coefficient for determining the two different results, until the error of the calibrated sand rate is below the pre-determined threshold.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
   a processing device; and
   a memory device that includes instructions executable by the processing device for causing the processing device to:
   receive real-time data including wellhead pressure, a new sand measurement, and a new erosion rate for a wellbore;
   calibrate a model including an available reference sand rate for the wellbore based on the wellhead pressure and at least one of the new sand measurement or the new erosion rate of the wellbore;
   apply the model to determine a calibrated sand rate is within a pre-determined threshold, wherein applying the model to determine the calibrated sand rate is within the pre-determined threshold includes:
   determining two different results for the calibrated sand rate using two different sand saturation levels and an initial erosion coefficient; and
   determining one of the two different results of the model is below the pre-determined threshold; and
   determine a new sand production rate for the wellbore based on the model.

2. The system of claim 1, wherein the memory device further includes instructions executable by the processing device for causing the processing device to:
   output a command to adjust a setting of a well tool used in a wellbore operation based on the new sand production rate.

3. The system of claim 1, wherein the model is configurable to calculate initial sand saturation levels, wherein the initial sand saturation levels are configurable to be roots of a quadratic relationship between sand saturation level values and available sand rate values from a reservoir simulator.

4. The system of claim 3, wherein the memory device further includes instructions executable by the processing device for causing the processing device to:
- in response to determining any of the results of the model is below the pre-determined threshold:
  - assume the calibrated sand rate, the sand saturation level associated with the calibrated sand rate, and the erosion coefficient for determining the new sand production rate.

5. The system of claim 3, wherein the instructions executable by the processing device for causing the processing device to apply the model to determine the calibrated sand rate is within the pre-determined threshold includes: determining one of the two different results of the calibrated sand rate is equal to or above the pre-determined threshold, and the memory device further includes instructions executable by the processing device for causing the processing device to:
- in response to determining one of the two different results of the model is equal to or above the pre-determined threshold:
  - apply the model using the calibrated sand rate with a minimum error, the sand saturation level associated with the calibrated sand rate with the minimum error, and a new erosion coefficient; and
  - determine the result of the model is below the pre-determined threshold.

6. The system of claim 4, wherein the instructions executable by the processing device for causing the processing device to apply the model to determine the calibrated sand rate is within the pre-determined threshold further includes:
- determining the result of the model using the calibrated sand rate with the minimum error is equal to or above the pre-determined threshold, and the memory device further includes instructions executable by the processing device for causing the processing device to:
- in response to determining the result of the model using the calibrated sand rate with the minimum error is equal to or above the pre-determined threshold:
  - re-apply the model using the calibrated sand rate with the minimum error, two new sand saturation levels, and the initial erosion coefficient for determining the two different results, until the error of the calibrated sand rate is below the pre-determined threshold.

7. A computer-implemented method comprising:
- receiving, by a processing device, real-time data including wellhead pressure, a new sand measurement, and a new erosion rate for a wellbore;
- calibrating, by the processing device, a model including an available reference sand rate for the wellbore based on the wellhead pressure and at least one of the new sand measurement or the new erosion rate of the wellbore;
- applying, by the processing device, the model to determine a calibrated sand rate is within a pre-determined threshold, wherein applying the model to determine the calibrated sand rate is within a pre-determined threshold includes:
  - determining, by the processing device, two different results for the calibrated sand rate using two different sand saturation levels and an initial erosion coefficient and
  - determining, by the processing device, one of the two different results of the model is below the pre-determined threshold; and
- determining, by the processing device, a new sand production rate for the wellbore based on the model.

8. The computer-implemented method of claim 7, further comprising:
- outputting, by the processing device, a command to adjust a setting of a well tool used in a wellbore operation based on the new sand production rate.

9. The computer-implemented method of claim 7, wherein the model is configurable to calculate, by the processing device, initial sand saturation levels, wherein the initial sand saturation levels are configurable to be roots of a quadratic relationship between sand saturation level values and available sand rate values from a reservoir simulator.

10. The computer-implemented method of claim 7, further comprising:
- in response to determining, by the processing device, any of the results of the model is below the pre-determined threshold:
  - assuming the calibrated sand rate, the sand saturation level associated with the calibrated sand rate, and the erosion coefficient for determining the new sand production rate.

11. The computer-implemented method of claim 7, wherein applying the model to determine the calibrated sand rate is within the pre-determined threshold includes:
- determining, by the processing device, one of the two different results of the calibrated sand rate is equal to or above the pre-determined threshold; and
- in response to determining, by the processing device, the result of the model using the calibrated sand rate with a minimum error is equal to or above the pre-determined threshold:
  - re-applying the model using the calibrated sand rate with the minimum error, two new sand saturation levels, and the initial erosion coefficient for determining the two different results, until the error of the calibrated sand rate is below the pre-determined threshold.

12. The computer-implemented method of claim 11, wherein applying the model to determine the calibrated sand rate is within the pre-determined threshold includes:
- determining, by the processing device, the result of the model using the calibrated sand rate with the minimum error is equal to or above the pre-determined threshold; and
- in response to determining, by the processing device, the result of the model using the calibrated sand rate with the minimum error is equal to or above the pre-determined threshold:
  - re-apply the model using the calibrated sand rate with the minimum error, two new sand saturation levels, and the initial erosion coefficient for determining the two different results, until the error of the calibrated sand rate is below the pre-determined threshold.

13. A non-transitory computer-readable medium comprising instructions that are executable by a processing device for causing the processing device to perform operations comprising:
- receiving real-time data including wellhead pressure, a new sand measurement, and a new erosion rate for a wellbore;
- calibrating a model including an available reference sand rate for the wellbore based on the wellhead pressure and at least one of the new sand measurement or the new erosion rate of the wellbore;
- applying the model to determine a calibrated sand rate is within a pre-determined threshold, wherein applying the model to determine the calibrated sand rate is within the pre-determined thresholds includes:

determining two different results for the calibrated sand rate using two different sand saturation levels and an initial erosion coefficient; and determining one of the two different results of the model is below the pre-determined threshold; and determining a new sand production rate for the wellbore based on the model.

14. The non-transitory computer-readable medium of claim 13, wherein the operations further comprise:

outputting a command to adjust a setting of a well tool used in a wellbore operation based on the new sand production rate.

15. The non-transitory computer-readable medium of claim 13, wherein the model is configurable to calculate initial sand saturation levels, wherein the initial sand saturation levels are configurable to be roots of a quadratic relationship between sand saturation level values and available sand rate values from a reservoir simulator.

16. The non-transitory computer-readable medium of claim 13, wherein the operations further comprise:

in response to determining any results of the model is below the pre-determined threshold:

assuming the calibrated sand rate, a sand saturation level associated with the calibrated sand rate, and the erosion coefficient for determining the new sand production rate.

17. The non-transitory computer-readable medium of claim 13, wherein the operation of applying the model to determine the calibrated sand rate is within the pre-determined threshold includes:

applying the model to determine the calibrated sand rate is within the pre-determined threshold includes:

determining one of the two different results of the calibrated sand rate is equal to or above the pre-determined threshold; and in response to determining the result of the model using the calibrated sand rate with a minimum error is equal to or above the pre-determined threshold:

re-applying the model using the calibrated sand rate with the minimum error, two new sand saturation levels, and the initial erosion coefficient for determining the two different results, until the error of the calibrated sand rate is below the pre-determined threshold.

* * * * *